(12) United States Patent
Hörnig

(10) Patent No.: US 7,113,836 B2
(45) Date of Patent: Sep. 26, 2006

(54) CONTROL DEVICE FOR MANEUVERING AN APPARATUS

(75) Inventor: Mathias Hörnig, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 44 days.

(21) Appl. No.: 11/070,501

(22) Filed: Mar. 2, 2005

(65) Prior Publication Data
US 2005/0195946 A1 Sep. 8, 2005

(30) Foreign Application Priority Data
Mar. 2, 2004 (DE) .................... 10 2004 010 205

(51) Int. Cl.
G05B 15/00 (2006.01)
G05B 19/18 (2006.01)
G09G 5/08 (2006.01)
G05G 9/00 (2006.01)
G05G 13/00 (2006.01)
G06F 17/00 (2006.01)
G06F 19/00 (2006.01)

(52) U.S. Cl. ............................ 700/85; 700/60; 700/61; 700/65; 700/66; 345/161; 74/471 R; 463/38; 378/210

(58) Field of Classification Search .................. 700/56, 700/60, 61, 65, 66, 83, 85; 345/156, 161; 463/36, 38; 348/211.7; 74/471 R; 89/45.15; 200/5; 273/148; 378/210; D14/412–414, D14/454, 117.4
See application file for complete search history.

(56) References Cited

U.S. PATENT DOCUMENTS

| 5,675,359 A | * | 10/1997 | Anderson ................... 345/161 |
| 6,043,806 A | * | 3/2000 | Atwell et al. .............. 345/161 |
| 6,059,660 A | * | 5/2000 | Takada et al. ............... 463/38 |
| 6,203,432 B1 | * | 3/2001 | Roberts et al. ............. 463/37 |
| 6,636,200 B1 | * | 10/2003 | Kataoka et al. ............ 345/161 |
| 2002/0052237 A1 | * | 5/2002 | Magill ....................... 463/38 |

FOREIGN PATENT DOCUMENTS

| DE | 100 16 180 C2 | 1/2002 |
| DE | 100 59 793 A1 | 6/2002 |
| DE | 101 60 389 A1 | 8/2002 |
| DE | 103 04 804 A1 | 8/2003 |
| EP | 1 343 113 A2 | 9/2003 |

OTHER PUBLICATIONS

"AXIOM Artis MP", [online], [retrieved on Feb. 24, 2004], 2 pages, Siemens.

(Continued)

Primary Examiner—Crystal J. Barnes

(57) ABSTRACT

Reliable and at the same time simple operation of a plurality of system components using only a single control element is guaranteed by means of the combination of a control lever (10) which can be swiveled manually and a rotational control unit (11) which can be rotated manually. Translatory control motions can be executed intuitively by means of swivel movements (16) of the control lever (10) and rotatory control motions can be executed intuitively by means of rotary movements (14) of the rotational control unit (11). The embodiment of the rotational control unit (11) in the form of a ring element surrounding the control lever (10), which can be can be adjusted by raising or lowering into different operating positions, associated in each case with a specific operating function, is particularly advantageous.

7 Claims, 1 Drawing Sheet

OTHER PUBLICATIONS

"AXIOM Artis FC/BC", [online], [retrieved on Feb. 24, 2004], 2 pages, Siemens.

"Inkrementale Handräder", Allgemein, Feb. 2004, 1 page.

"AXIOM Artis dTA—Lösungen statt Kompromisse", Das deckengehängte Angiographie-System mit Flachdetektor-Technologie, Siemens Medical, Feb. 2004, 3 pages.

"AXIOM Artis dFC and AXIOM Artis dBC", The all-digital cath lab systems with Flat Panel Detector Technology, Siemens Medical, Feb. 2004, 2 pages.

"Interventions and 3D imaging—without compromises", Siemens Medical, Feb. 2004, 2 pages.

* cited by examiner

CONTROL DEVICE FOR MANEUVERING AN APPARATUS

CROSS REFERENCE TO RELATED APPLICATIONS

This application claims priority to the German application No. 10 2004 010 205.8, filed Mar. 2, 2004 which is incorporated by reference herein in its entirety.

FIELD OF INVENTION

The invention relates to a control element, particularly for controlling a medical system, having a control lever which can be swiveled manually.

BACKGROUND OF INVENTION

X-ray systems which are used for example in cardiological examinations contain different system components, in particular an electrically adjustable X-ray table, an X-ray stand, a detector and an X-ray source. Before an examination begins, each of these system components must be set to a position predefined by the examination. In this situation, the setting of the system component in question is performed as a rule from a control panel which is located close to the patient on the examination table.

Such a control panel, also mentioned in the aforementioned case, for controlling the system components of an X-ray system has different discrete control elements assigned to the system components. Prior to the commencement of an examination, the individual system components are set by means of the control elements assigned to them to a defined position during preparations for the examination. In this situation, the precise positional setting of the X-ray table is performed by means of a control lever which can be swiveled manually as a first discrete control element, whereby translatory control motions are associated with the swiveling movements of this control lever; the precise positional setting of the X-ray stand is performed by means of a rotational control unit which can be turned manually as a second discrete control element, whereby rotatatory control motions are associated with the rotary movements of this rotational control unit. With regard to the operation of different system components, it is necessary for the user to maintain visual contact with the control panel when switching operation between the system components in order to avoid the danger of an operating error as a result of an incorrect manual action.

Control elements are known from the technical field of motor vehicle technology which comprise different types of control units.

A multifunction control facility for a motor vehicle having a plurality of control elements capable of being actuated in the axial direction of the control facility, for example, is known from DE 100 59 793 A1, whereby the multifunction control facility additionally has a bidirectionally rotatable setting ring which is implemented separately from said facility.

A further control medium in which a plurality of control elements are combined with one another is known from DE 103 04 804 A1. The known control medium has a rotary ring which can be brought into a rotary position as a first control element and second control element which can be brought into a swivel position and a slide position, whereby a switch position is assigned to each rotary position, swivel position and slide position.

In addition, an electrical switch having a swiveling actuation element in the manner of a joystick and a further switch element which can be brought into a rotary position are known from DE 101 60 389 A1, such that a menu selection or parameter input can be made on a screen in the motor vehicle.

EP 1 343 113 A2 likewise discloses a control element for motor vehicles which is located in the vicinity of the driver's seat, whereby the control element has a joystick and a rotary wheel located separately from the latter for cursor control purposes.

Furthermore, a swiveling multifunction control element in the manner of a joystick having a ring element is known from DE 100 16 180 C2, whereby the ring element can be rotated in one sense of rotation in order to set an input value and can be actuated in the axial direction by pulling or pushing in order to confirm the previously set input value.

SUMMARY OF INVENTION

An object of the present invention is to develop a control element, particularly for operating a medical system, in such a way as to guarantee greater flexibility whilst simultaneously offering high reliability levels in the operation of a plurality of components in a system.

This object is achieved by the claims; advantageous embodiments of the control element are set down in the dependent claims.

A ring element of a control element, which can be adjusted by raising or lowering into different operating positions, associated in each case with a specific control motion, makes possible the simple and nevertheless reliable operation, also on an individual basis, of a plurality of system components through the use of only a single control element which can be moved manually.

With regard to a switch in operation between the system components, in the case of the combined control element according to the invention there is no need to reposition the hand from one discrete control element to a further discrete control element separated spatially from the first. The danger of operating the system incorrectly as a result of accidentally actuating a control element when repositioning the hand is therefore avoided with this combined control element. A user can moreover operate the different system components without needing to have visual contact with the combined control element and can concentrate to a greater degree on the positioning task, in contrast to the known control panels.

The combined control element according to the invention ensures intuitive operation of a system particularly advantageously as a result of the fact that a translatory or rotatory control motion to be performed can be achieved in each case by means of a synchronous form of operation using only a single control element. Swivel movements of the manually guided control lever are associated with the form of motion synchronized with this of a translatory control motion, while rotational movements of the manually guided rotational control unit are associated with the form of motion synchronized with this of a rotatory control motion.

A particularly operator-friendly and at the same time simple embodiment of the rotational control unit from the design viewpoint with regard to the combined control element according to the invention is given by the form of at least one ring element surrounding the control lever and rotationally adjustable with respect to the latter, with the result that simultaneous or consecutive positionally accurate control can be exercised over translatory control motions by means of the manually guided control lever and over rotatory control motions by means of a ring element guided by at least one finger.

According to one embodiment of the invention, the control functionality of the rotational control unit according to the invention in the form of a ring element can additionally be extended in that the rotational control unit can be adjusted by raising or lowering into different operating positions, associated in each case with a specific control motion, and/or can be fixed.

An indexing predefined in the direction of rotation in a further embodiment for the rotational motion of the rotational control unit in the combined control element according to the invention ensures incremental and positionally accurate setting of an angle of rotational adjustment for the rotational control unit.

BRIEF DESCRIPTION OF THE DRAWINGS

The invention and also further advantageous embodiments of the invention in accordance with the subclaims are described in more detail below with reference to an exemplary embodiment represented schematically in the drawings, in which;

DETAILED DESCRIPTION OF INVENTION

Figure 1:
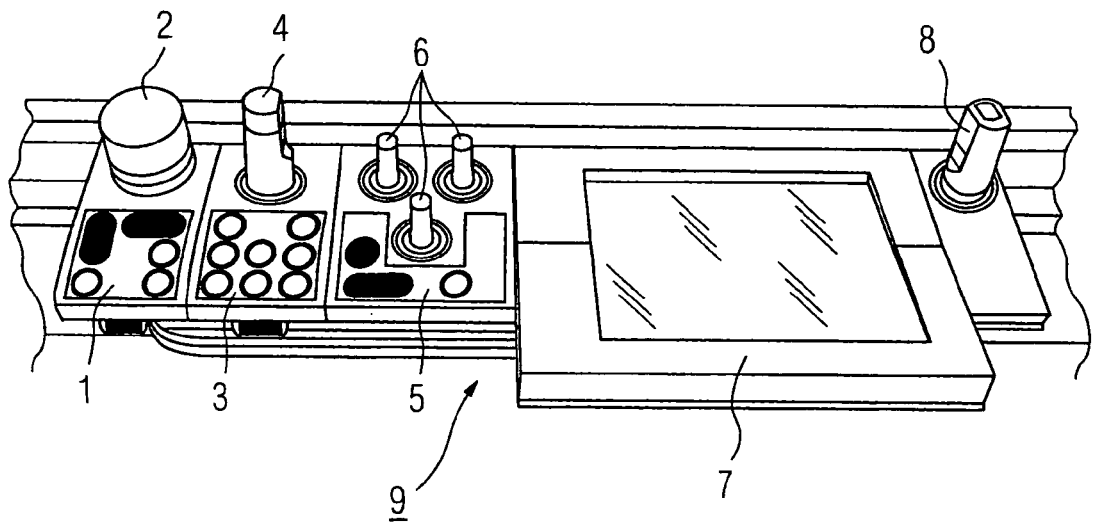
FIG. 1 shows a known control panel for controlling an X-ray system having the discrete control elements for an X-ray table, an X-ray stand, a collimator and an image system.

FIG. 1 shows a known control panel 9 of a medical X-ray system for controlling the system components not shown in the figure, such as for controlling an electrically adjustable X-ray table, an X-ray stand, a collimator and an image system, for example. In this situation, a discrete control element is assigned to each respective system component. The discrete control element 1 with a rotational control unit 2 is assigned to the X-ray table, the discrete control element 3 with the swiveling control lever 4 is assigned to the X-ray stand, the discrete control element 5 with a group of swiveling control levers 6 is assigned to the collimator, and a further control element 7 with an additional control lever 8 is assigned to the image system. During preparations for the examination, the system components are set successively by means of the aforementioned discrete control elements which can be operated manually to a position which is specific to the examination or to a parameter value which is specific to the examination.

With regard to a switch in operation between the discrete control elements, it is necessary to reposition the hand from the one discrete control element to another appropriate discrete control element. As a result of the spatial separation of the discrete control elements 1,3,5 and 7 the user must establish visual contact with the control panel 9 in order to thus exclude the danger of incorrect operation as a result of accidentally actuating one of the control levers 4,6,8 or the rotational control unit 2.

Figure 2:
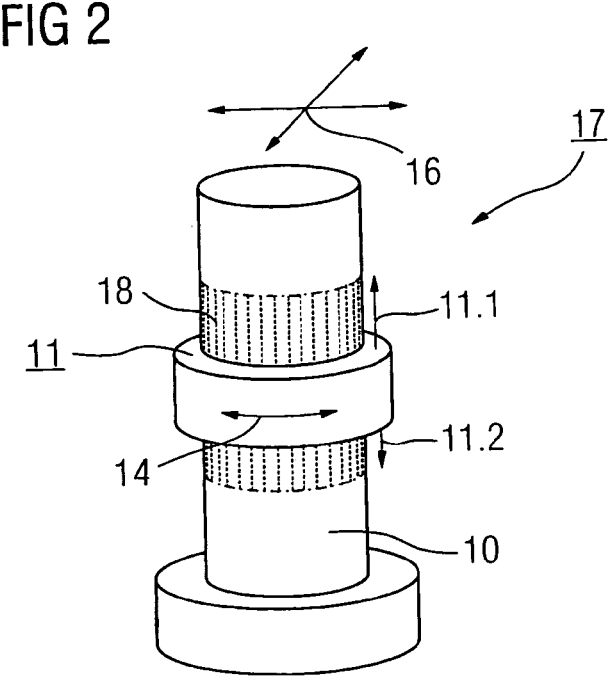
FIG. 2 shows a control unit according to the invention having a combination of a manually guided control lever and a manually guided rotational control unit.

FIG. 2 shows a combined control element 17 according to the invention which can be operated manually, in which a swiveling control lever 10 is combined with a rotatable rotational control unit 11 in the form of a ring element surrounding the control lever. On the one hand the control lever 10 of the combined control element 17 replaces the control lever 4 of the discrete control element 1 shown in FIG. 1 and on the other hand the rotational control unit 11 of the combined control element 17 replaces the rotational control unit 2 of the second discrete control element 3 shown in FIG. 1.

As a result of combining different discrete control elements to form one combined control element 17 which can be operated manually, a reliable switch in operation between the system components is guaranteed without needing to reposition the operating hand and without the operator needing to have visual contact with the control element 17, so that the danger of operating the system incorrectly as a result of accidentally actuating a control element can be avoided. As a result of the combination of a control lever 10 which can be swiveled manually with a rotational control unit 11 which can be rotated manually, translatory control motions can be executed particularly intuitively by means of an appropriate synchronous swivel movement 16 of the control lever 10 and rotatory control motions can be executed particularly intuitively by means of an appropriate synchronous rotary movement 14 of the rotational control unit 11.

The rotational control unit 11 can be adjusted by raising or lowering into different operating positions 11.1 or 11.2, to which specific control functions are assigned, thus enabling the user to switch in a simple manner between the operation of different system components without having to change the manual grip.

In one embodiment of the invention, the setting for the angle of rotation for the rotational control unit 11 can be fixed by raising or lowering into the operating positions 11.1 or 11.2 respectively in order to avoid accidental variation of the angle of rotation. The fixed setting can be canceled again at any time by shifting the rotational control unit 11 back to its original position.

In a further embodiment of the invention, the rotational control unit 11 has an indexing 18 in the direction of the rotary movement 14 for the purposes of positionally accurate and sensitive setting of the angle of rotation. The indexing 18 can be achieved both mechanically, for example by means of an appropriate design of the contact surface between rotational control unit 11 and control lever 10, and also electromechanically, for example through the generation of appropriate magnetic fields between the rotational control unit 11 and the control lever 10.

The combined control element 17 according to the invention can be used particularly advantageously for controlling the different system components of an X-ray system.

The essential concept of the invention can be summarized as follows:

Reliable and at the same time simple operation of a plurality of system components using only a single control element is guaranteed by means of the combination of a control lever (10) which can be swiveled manually and a rotational control unit (11) which can be rotated manually. Translatory control motions can be executed intuitively by means of swivel movements (16) of the control lever (10) and rotatory control motions can be executed intuitively by means of rotary movements (14) of the rotational control unit (11). The embodiment of the rotational control unit (11) in the form of a ring element surrounding the control lever (10), which can be can be adjusted by raising or lowering into different operating positions, associated in each case with a specific operating function, is particularly advantageous.

The invention claimed is:

1. A control device for maneuvering an apparatus, comprising:
    a swivel-mounted control handle adapted to be operated manually; and
    a control element shaped as a ring encircling the control handle, wherein the control element is adapted to be actuated by:
    rotating the control element relative to the control handle,
    pulling or pressing the control handle along a longitudinal axis of the control handle, and
    raising or lowering the control element to a plurality of different pre-defined setting positions of the control element each corresponding to a specific maneuvering movement of the apparatus.

2. The control device according to claim 1, wherein the control device is adapted to effect a translatory maneuvering movement of the apparatus by swiveling the control handle.

3. The control device according to claim 1, wherein the control device is adapted to effect a rotational maneuvering movement of the apparatus by rotating the control element.

4. The control device according to claim 1, wherein the control element is adapted to be fixed in a current setting position of the control element by raising or lowering the control element to the current setting position.

5. The control device according to claim 1, wherein the control element includes a focusing scale representing a rotation angle for incrementally rotating the apparatus by setting the control element to a desired rotation angle relative to the focusing scale.

6. A medical examination or treatment system, comprising a control device for maneuvering the medical examination or treatment system, the control device comprising:
    a swivel-mounted control handle adapted to be operated manually; and
    a control element shaped as a ring encircling the control handle, wherein the control element is adapted to be actuated by:
    rotating the control element relative to the control handle,
    pulling or pressing the control handle along a longitudinal axis of the control handle, and
    raising or lowering the control element to a plurality of different pre-defined setting positions of the control element each corresponding to a specific maneuvering movement of the apparatus.

7. The medical examination or treatment system according to claim 6, wherein the medical examination or treatment system is a medical X-ray device.

* * * * *